(12) United States Patent
Sato et al.

(10) Patent No.: US 9,269,477 B2
(45) Date of Patent: Feb. 23, 2016

(54) MULTI-CORE CABLE

(71) Applicant: SUMITOMO ELECTRIC INDUSTRIES, LTD., Osaka-shi, Osaka (JP)

(72) Inventors: Kazuhiro Sato, Kanuma (JP); Masato Tanaka, Kanuma (JP); Tatsunori Hayashishita, Aomori (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 13 days.

(21) Appl. No.: 13/926,180

(22) Filed: Jun. 25, 2013

(65) Prior Publication Data

US 2013/0341065 A1    Dec. 26, 2013

(30) Foreign Application Priority Data

Jun. 26, 2012  (JP) ................................ 2012-142770
Jun. 28, 2012  (JP) ................................ 2012-145002

(51) Int. Cl.
*H01B 11/18*    (2006.01)
*H01B 7/04*     (2006.01)
*A61B 1/00*     (2006.01)

(52) U.S. Cl.
CPC ............ *H01B 11/1895* (2013.01); *H01B 7/048* (2013.01); *A61B 1/00114* (2013.01)

(58) Field of Classification Search
CPC .......... B21B 1/46; C22C 21/00; C22C 21/06; C22C 21/10; H01B 7/00; H01B 7/20; H01B 11/1895; H01B 11/1808; H01B 11/18; H01B 11/02; H01B 7/048; H01B 7/04; G02B 6/44; A61B 1/00114; H01R 13/50; H02P 25/16; H05K 9/00

USPC .......... 174/113 R, 115, 350, 107, 109, 105 R, 174/36, 34; 333/4; 439/399, 354, 404, 497, 439/579, 607; 339/177, 176 MF, 107, 115, 339/117 F; 318/400.41; 156/51, 53, 56

See application file for complete search history.

(56) References Cited

U.S. PATENT DOCUMENTS

| | | | | |
|---|---|---|---|---|
| 3,291,891 A | * | 12/1966 | Sharp | 174/36 |
| 4,674,822 A | * | 6/1987 | Hall | 439/399 |
| 4,761,519 A | * | 8/1988 | Olson et al. | 174/107 |
| 5,548,082 A | * | 8/1996 | Palmer | 174/34 |

(Continued)

FOREIGN PATENT DOCUMENTS

| | | |
|---|---|---|
| CN | 101110283 A | 1/2008 |
| CN | 101325099 A | 12/2008 |

(Continued)

OTHER PUBLICATIONS

Korean Office Action for 10-2013-0073081 dated Sep. 18, 2014.

(Continued)

*Primary Examiner* — Timothy Thompson
*Assistant Examiner* — Guillermo Egoavil
(74) *Attorney, Agent, or Firm* — Global IP Counselors, LLP

(57) ABSTRACT

One embodiment provides a multi-core cable including: at least one ground wire which is arranged in a center or its vicinity in a cross section perpendicular to a length direction of the cable; plural insulated wires arranged in a periphery of the ground wire; an overall shield layer which covers a periphery of the insulated wires; and a sheath which covers a periphery of the overall shield layer.

7 Claims, 3 Drawing Sheets

(56) References Cited

U.S. PATENT DOCUMENTS

| | | | |
|---|---|---|---|
| 6,417,445 B1* | 7/2002 | Sato et al. | 174/36 |
| 7,323,640 B2 | 1/2008 | Takahashi et al. | |
| 8,546,690 B2* | 10/2013 | Masakazu et al. | 174/103 |
| 2010/0097023 A1* | 4/2010 | Nakamura et al. | 318/400.41 |
| 2010/0236810 A1* | 9/2010 | Mukai et al. | 174/105 R |
| 2010/0236812 A1* | 9/2010 | Laudenslager et al. | 174/113 R |
| 2010/0239029 A1* | 9/2010 | Komori | H01Q 1/242 375/257 |
| 2011/0162866 A1 | 7/2011 | Masakazu et al. | |
| 2012/0292079 A1* | 11/2012 | Muramatsu et al. | 174/113 R |

FOREIGN PATENT DOCUMENTS

| | | |
|---|---|---|
| CN | 101523514 A | 9/2009 |
| CN | 201477988 U | 5/2010 |
| JP | 2001-023456 A | 1/2001 |
| JP | 2002-515632 A | 5/2002 |
| KR | 1020050021539 A | 3/2005 |
| KR | 10-2001-0015137 A | 1/2007 |
| TW | 480498 B | 3/2002 |
| TW | 201014089 A | 4/2010 |
| TW | M419200 U | 12/2011 |

OTHER PUBLICATIONS

Taiwanee Office Action for 102122301 dated Nov. 10, 2014.
Office Action in the corresponding Chinese Patent Application No. 201310259474.3 dated Jun. 23, 2015.
Office Action in the corresponding Korean Patent Application No. 10-2013-0073081 dated Oct. 26, 2015.

* cited by examiner

MULTI-CORE CABLE

CROSS-REFERENCE TO RELATED APPLICATION(S)

This application claims priorities from Japanese Patent Application No. 2012-142770 filed on Jun. 26, 2012 and from Japanese Patent Application No. 2012-145002 filed on Jun. 28, 2012, the entire contents of which are incorporated herein by reference.

FIELD

The present invention relates to a multi-core cable having a ground wire and plural insulated wires.

BACKGROUND

For high-frequency transmission, a multi-core cable in which plural coaxial cables are collected inside a sheath member having flexibility is known (for example, see JP-2001-023456-A).

Such multi-core cable may be used in medical devices such as a catheter, an endoscope or a probe cable for ultrasonograph, and thus, further reduction in diameter thereof is desired in order to improve workability or handleability of the cable to thereby reduce a stress for a patient to be treated with the endoscope etc.

SUMMARY

An object of the invention is to provide a multi-core cable having good electrical characteristics while enabling a reduction in diameter.

One aspect of the invention provides a multi-core cable including:

at least one ground wire which is arranged in a center or its vicinity in a cross section perpendicular to a length direction of the cable;

plural insulated wires arranged in a periphery of the ground wire;

an overall shield layer which covers a periphery of the insulated wires; and a sheath which covers a periphery of the overall shield layer.

In the multi-core cable, the ground wire may be arranged in the center in the cross section, and the overall shield layer and the ground wire may be coaxial.

In the multi-core cable, the insulated wires may be arranged in plural layers so that each layer is coaxial with the ground wire.

Another aspect of the present invention provides a multi-core cable including:

plural wire units, each wire unit being the above-mentioned multi-core cable;

another overall shield layer which collectively covers a periphery of the plural wire units; and another sheath which covers a periphery of the another overall shield layer.

In the multi-core cable, the ground wire may be another insulated wire, and a terminal processing may be performed so as to ground the ground wire and the overall shield layer.

In the multi-core cable, at least two of the insulated wires as the ground wires may be provided.

In the multi-core cable, the ground wire may be a conductor wire, another conductor wire and the insulated wires may be arranged in a layer around the ground wire, and the another conductor wire may electrically connect the ground wire and the overall shield layer.

According to the invention, the ground wire arranged in the center or its vicinity in the cross section of the cable and the overall shield layer are coaxial, thereby providing the multi-core cable having good electrical characteristics in terms of practicality with a reduced diameter.

DETAILED DESCRIPTION

Embodiment 1

A multi-core cable of Embodiment 1 will hereinafter be described with reference to the drawings.

Figure 1:
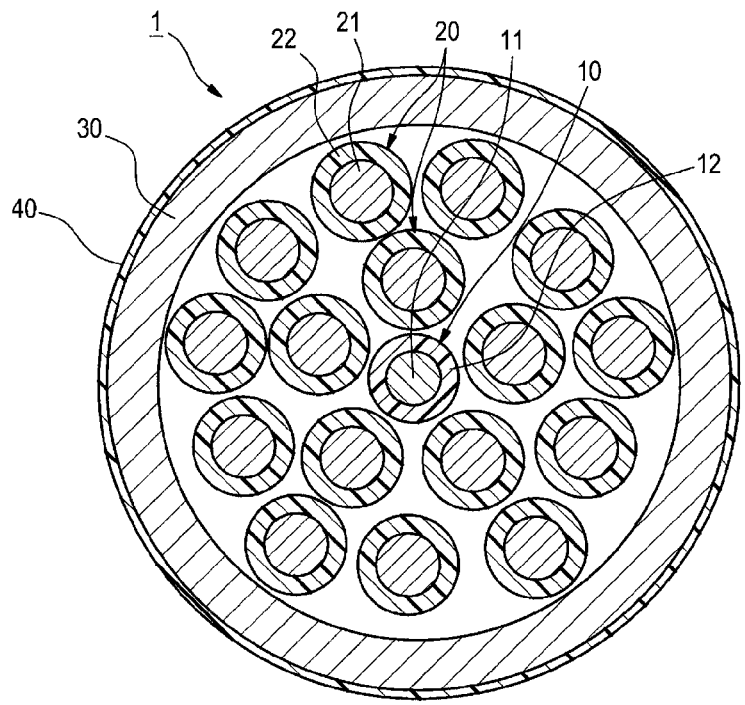
FIG. 1 cross-sectionally shows a multi-core cable of Embodiment 1.

As shown in FIG. 1, a multi-core cable 1 of Embodiment 1 includes a ground wire 10, plural insulated wires 20, an overall shield layer 30 which covers the ground wire 10 and the insulated wires 20, and a sheath 40 which covers the periphery of the overall shield layer.

The ground wire 10 is constructed of a central conductor 11 and an insulating coating 12 which covers the periphery of the central conductor 11. In Embodiment 1, the ground wire 10 uses, for example, an AWG 42 (American Wire Gauge number 42) wire. The central conductor 11 of the ground wire 10 is not necessarily covered with the coating 12. However, when the central conductor 11 is covered with the coating 12, for example, the central conductor of the ground wire 10 and a central conductor 21 of the insulated wire 20 described below can be prevented from being short-circuited due to friction between the ground wire 10 and the peripheral insulated wires 20.

As the central conductor 11 of the ground wire 10, for example, a twisted wire is used. For example, in the case of twisting seven tin-plated annealed copper wires or silver-plated annealed copper wires with a conductor diameter of 0.025 mm, a twisted wire with an outside diameter of 0.075 mm is obtained.

As a material of the coating 12 of the ground wire 10, it is preferable to use a fluorine resin such as a perfluoroalkoxy resin (PFA) with good heat resistance, chemical resistance, non-adhesion, self-lubricity, etc. The coating 12 is formed by extruding this fluorine resin or winding a fluorine resin tape, and an outside diameter of the coating 12 is, for example, 0.20 mm.

In this multi-core cable 1, the ground wire 10 is arranged in the center in a cross section (cross section shown in FIG. 1) perpendicular to a length direction of the cable. And, the plural (16 herein) insulated wires 20 are arranged around this ground wire 10. An intervening substance such as aramid fiber or spun rayon yarn may be provided in a gap between the ground wire 10 and the insulated wires 20.

Each of the insulated wires 20 is constructed of a central conductor 21 and an insulating coating 22 which covers the periphery of the central conductor 21. In Embodiment 1, the central conductor 21 of the insulated wire 20 is the AWG 42 (American Wire Gauge number 42) wire.

Like the central conductor 11 of the ground wire 10, as the central conductor 21 of the insulated wire 20, for example, a twisted wire with an outside diameter of 0.075 mm obtained by twisting seven silver-plated annealed copper wires with a conductor diameter of 0.025 mm is used.

As a material of the coating 22 of the insulated wire 20, it is preferable to use a material similar to that of the coating 12 of the ground wire 10. An outside diameter of the coating 22 is, for example, 0.26 mm slightly larger than the outside diameter of the coating 12.

As shown in FIG. 1, for example, the five insulated wires 20 may be arranged around the ground wire 10 as a first layer and the eleven insulated wires 20 are arranged around the first layer as a second layer. That is, the insulated wires 20 may be arranged in plural layers so that each of the first and second layers are coaxial with the ground wire 10.

The insulated wires 20 may be twisted respectively for the first layer and the second layer. Or, the ground wire 10 and all the insulated wires 20 may be collectively twisted so as to maintain a relative positional relationship between the insulated wires 20 and the ground wire 10.

The periphery of the ground wire 10 and the plural insulated wires 20 arranged in this manner is covered with the overall shield layer 30. The overall shield layer 30 is formed by spirally winding, for example, plural (79 herein) tin-plated annealed copper wires with a conductor diameter of 0.05 mm on the periphery of the ground wire 10 and the insulated wires 20, and an outside diameter of the overall shield layer 30 is, for example, 1.32 mm. The overall shield layer 30 may be constructed by braiding small-diameter metal wires.

The outer periphery of this overall shield layer 30 is further covered with the sheath 40. The sheath 40 is formed by wrapping, for example, a resin tape made of polyethylene terephthalate (PET) with a thickness of 4 μm on the periphery of the overall shield layer 30.

In the multi-core cable 1 of Embodiment 1 including one AWG 42 ground wire 10 and 16 AWG 42 insulated wires 20, an outside diameter of the sheath 40 is, for example, 1.34 mm.

The sheath 40 may be obtained by extruding and coating polyvinyl chloride (PVC), polyolefin or fluorine resin, instead of using a resin tape.

In Embodiment 1, the ground wire 10 arranged in the center in a cross section of the cable is coaxial with the overall shield layer 30 which covers the periphery of the insulated wires 20. Consequently, the multi-core cable 1 itself functions as a coaxial cable.

In addition, both ends of the ground wire 10 and both ends of the overall shield layer 30 are respectively grounded to the outside.

As described above, an insulated conductive wire is constructed of a central conductor and an insulating coating which covers the periphery of the central conductor. On the other hand, a coaxial wire further includes an external conductor which covers the periphery of the insulating coating and a protective coating which covers the external conductor, in addition to a configuration (the central conductor and the inside insulating coating) of the insulated conductive wire. Consequently, in the case of using a coaxial wire as each core wire like a conventional multi-core cable, an outside diameter of each core wire (coaxial wire) becomes larger than the case of using an insulated conductor as each core wire. Accordingly, an outside diameter of the multi-core cable also becomes larger.

An outside diameter of the multi-core cable 1 of Embodiment 1 including 16 AWG 42 insulated wires 20 is, for example, 1.34 mm. On the other hand, an outside diameter of an outermost sheath of the conventional multi-core cable including the same number (16) of AWG 42 coaxial wires is, for example, 1.55 mm.

Figure 5:
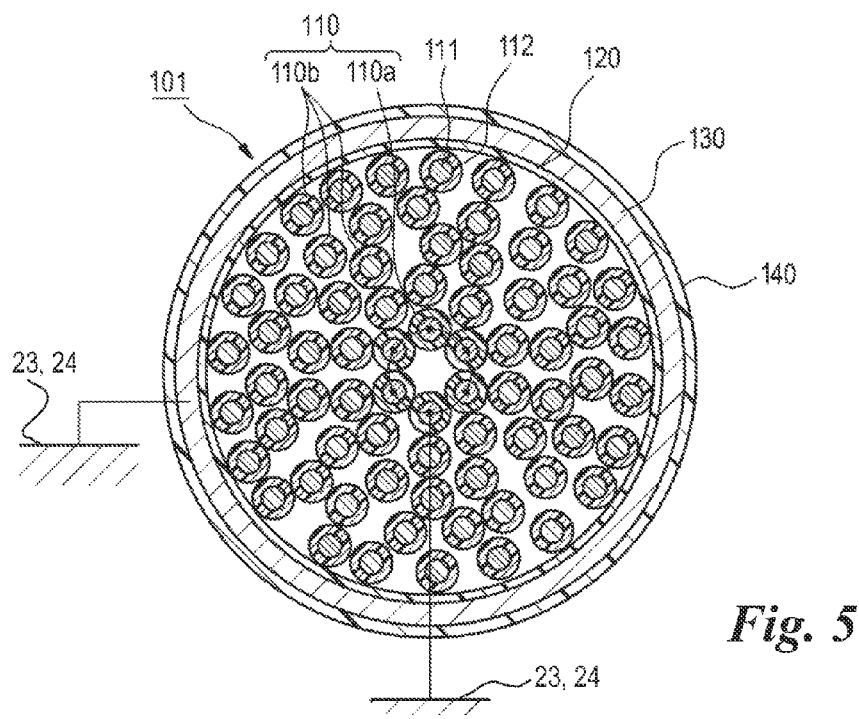
FIG. 5 cross-sectionally shows a multi-core cable of Embodiment 8.
Figure 6:
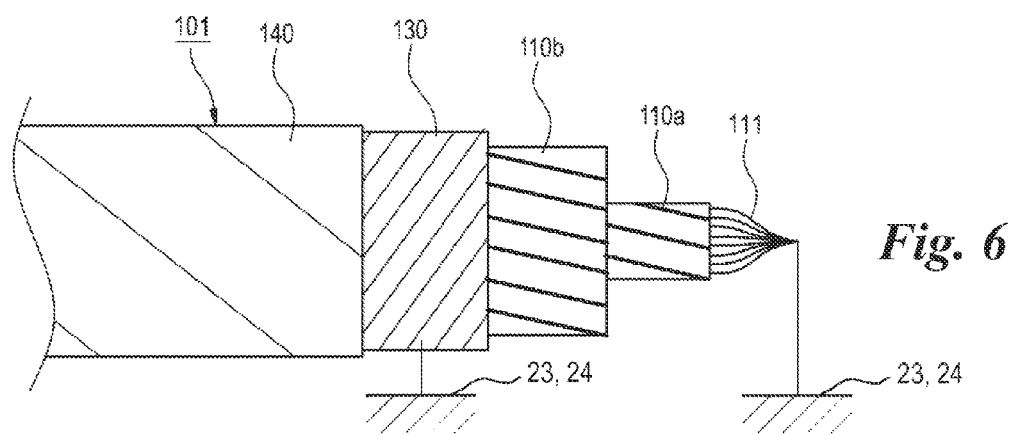
FIG. 6 shows terminal processing of the multi-core cable of Embodiment 8 from side.

The multi-core cable 1 of Embodiment 1 is smaller in diameter than the conventional multi-core cable using the coaxial wire as each core wire. As a result, handleability of the cable is improved and also, workability in the case of connecting the terminal of the cable to a wiring substrate of a medical device such as an ultrasonograph is improved. An example of a ground terminal 23 of the wiring substrate is shown in FIGS. 5 and 6. Further, a stress for a patient to be treated with an endoscope can be reduced.

Also, the multi-core cable 1 of Embodiment 1 has a pseudo coaxial structure by respectively grounding the ground wire 10 and the overall shield layer 30 which are coaxial, thereby providing good electrical characteristics for practical use in terms of characteristic impedance, capacitance, shielding properties, etc.

Although one embodiment is described above, the invention is not limited thereto, and other configurations can be adopted as necessary.

For example, the numbers of ground wires 10 and insulated wires 20 in the multi-core cable 1 are not limited to those of Embodiment 1. Also, in Embodiment 1, the outside diameter of the ground wire 10 is set smaller than the outside diameter of the insulated wire 20, but instead of this, the outside diameter of the ground wire 10 may be set substantially equally to the outside diameter of the insulated wire 20, or the outside diameter of the ground wire 10 may be set larger than the outside diameter of the insulated wire 20.

Although the periphery of the central conductor 11 of the ground wire 10 is covered with the coating 12 in Embodiment 1, the coating 12 may be omitted since the ground wire 10 is merely to be grounded.

In Embodiment 1, as the coating 12 of the ground wire 10 and the coating 22 of the insulated wire 20, the fluorine resin such as the perfluoroalkoxy resin (PFA) is used, but the coating 12, 22 may be a foam, and in order to better improve electrical characteristics, for example, a metal tape may be wound on a surface of the coating 12, 22, or the surface may be plated with metal. The insulated wires 20 of an outermost layers may be wrapped with a resin tape such as a PET tape, inside the overall shield layer 30.

Embodiment 2

In Embodiment 1, the twisted wire obtained by twisting seven silver-plated annealed copper wires is used as the central conductor 11 of the ground wire 10 and the central conductor 21 of the insulated wire 20, but instead of this, for example, a copper alloy wire of a single wire with an outside diameter of 0.064 mm may be used. Similarly in this case, when setting an outside diameter of a coating 12 of a ground wire 10 at 0.20 mm and setting an outside diameter of a coating 22 of an insulated wire 20 at 0.26 mm, an outside diameter of an outermost sheath 40 is, for example, 1.34 mm, and a multi-core cable with a diameter smaller than that of a conventional multi-core cable using a coaxial wire as each core wire can be obtained.

Embodiment 3

In Embodiment 1 and Embodiment 2, the AWG 42 wire is used as the ground wire 10 and the insulated wire 20, but instead of this, an AWG 40 wire may be used.

In a multi-core cable of Embodiment 3, one AWG 40 ground wire 10 is arranged in the center, and five AWG 40 insulated wires 20 are arranged in the periphery of the ground wire 10 as a first layer, and eleven AWG 40 insulated wires 20 are further arranged in the periphery of the first layer as a second layer.

In Embodiment 3, as a central conductor 11 of the ground wire 10, for example, a twisted wire with an outside diameter of 0.09 mm obtained by twisting seven tin-plated copper alloy wires with a conductor diameter of 0.03 mm is used. An outside diameter of a coating 12 of the ground wire 10 is, for example, 0.25 mm.

As a central conductor 21 of the insulated wire 20, for example, a twisted wire with an outside diameter of 0.09 mm obtained by twisting seven tin-plated copper alloy wires with a conductor diameter of 0.03 mm is used. An outside diameter of a coating 22 of the insulated wire 20 is, for example, 0.31 mm.

An overall shield layer 30 may be formed by spirally winding, for example, plural (about 94 herein) tin-plated annealed copper wires with a conductor diameter of 0.05 mm on the periphery of the ground wire 10 and the insulated wires 20 and in that case, an outside diameter of the overall shield layer 30 is, for example, 1.55 mm.

Also, an outside diameter of a sheath 40 formed by a resin tape made of polyethylene terephthalate (PET) with a thickness of 4 μm is, for example, 1.57 mm.

On the other hand, an outside diameter of an outermost sheath of a conventional multi-core cable collecting the same number (16) of AWG 40 coaxial wires as the number of insulated wires 20 included in the multi-core cable of Embodiment 3 is, for example, 1.83 mm.

Consequently, the multi-core cable of Embodiment 3 using the AWG 40 insulated wires is also smaller in diameter than the conventional multi-core cable formed by collecting plural AWG 40 coaxial wires, and is suitable as the multi-core cable used in a medical device etc.

Embodiment 4

In Embodiment 3, the twisted wire obtained by twisting seven tin-plated copper alloy wires is used as the central conductor 11 of the ground wire 10 and the central conductor 21 of the insulated wire 20, but instead of this, for example, a copper alloy wire of a single wire with an outside diameter of 0.08 mm may be used. In this case, similarly to Embodiment 3, when setting an outside diameter of a coating 12 of a ground wire 10 at 0.25 mm and setting an outside diameter of a coating 22 of an insulated wire 20 at 0.31 mm, an outside diameter of an outermost sheath 40 is, for example, 1.57 mm, and a multi-core cable with a diameter smaller than that of a conventional multi-core cable using a coaxial wire as each core wire can be obtained.

Embodiment 5

In Embodiment 1 and Embodiment 2, the AWG 42 wire is used as the ground wire 10 and the insulated wire 20, but instead of this, an AWG 32 wire covered with PFA may be used as a ground wire 10, and eight AWG 40 insulated wires 20 may be arranged in the periphery of the ground wire 10. In this case, an overall shield layer 30 is formed by spirally winding a tin-plated copper alloy wire, and a sheath 40 is formed by wrapping a resin tape made of polyester on the periphery of the overall shield layer 30.

As a result of measuring electrical characteristics of a multi-core cable 1 in Embodiment 5, characteristic impedance was 94Ω at a frequency of 10 MHz and capacitance was 64 pF/m. Also, a signal attenuation rate was 0.383 dB/m at the frequency of 10 MHz. These characteristics are sufficient practically as a coaxial cable of this size.

Comparative Example

As Comparative Example, a multi-core cable having an outside diameter substantially equal to that of the multi-core cable 1 of Embodiment 5 was manufactured using a coaxial wire. Assuming that outside diameters are the same, a central conductor of a coaxial wire is smaller than a central conductor of an insulated wire. Thus, the central conductor of the coaxial wire in Comparative Example is smaller than that of the central conductor of the ground wire 10 or the insulated wire 20 in Embodiment 5. As a result, a measured signal attenuation rate in the multi-core cable of Comparative Example was 0.470 dB/m which is higher than that in the multi-core cable 1 of Embodiment 5.

Conversely, according to Embodiment 5, the multi-core cable 1 having good electrical characteristics (low signal attenuation rate) can be obtained.

Embodiment 6

As a ground wire, a conductor wire having no cover may be used, and at least one conductor wire may be included in a layer of plural insulated wires arranged around the ground wire, so that the ground wire is electrically connected with an overall shield layer via the conductor wire.

Figure 2:
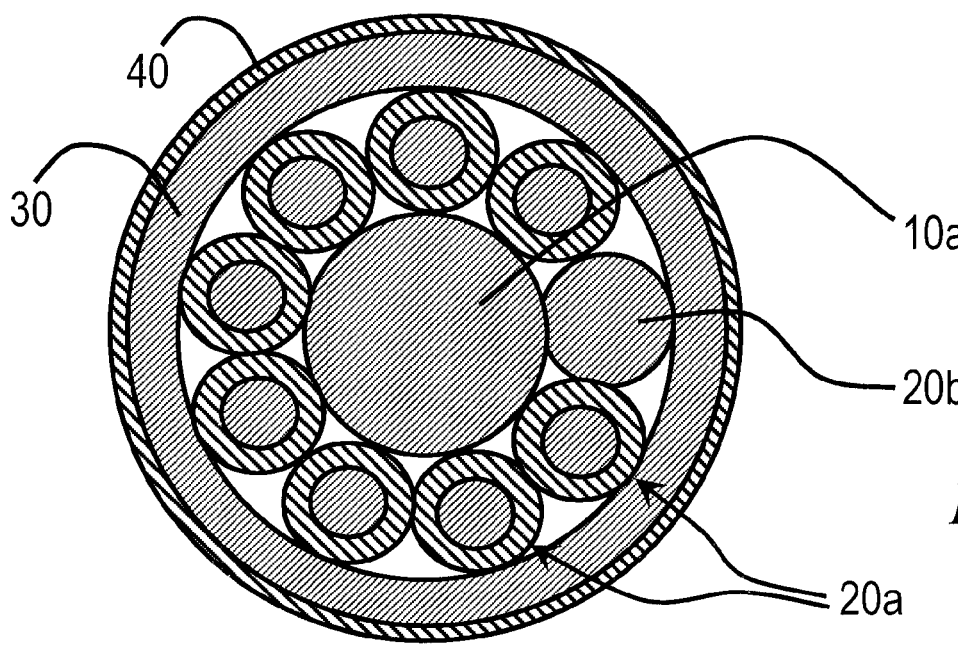
FIG. 2 shows one example of a multi-core cable of Embodiment 6.

In Embodiment 6, as shown in FIG. 2, a ground wire 10a consisting of a conductor wire is arranged at a center, and plural insulated wires 20a are arranged around the ground wire 10a. Further, a conductor wire 20b is arranged in the layer of the insulated wires 20a. Thus, the ground wire 10a and the overall shield layer 30 are electrically connected with each other through the conductor wire 20b. A diameter of the conductor wire 20b may be set to be equal to or slightly larger than a diameter of each of the insulated wires 20a.

When the overall shield layer 30 is constructed by braided plural metal wires, it is necessary to bundle these plural metal wires for grounding the overall shield layer 30. Such operation of bundling plural metal wires is troublesome. However, in Embodiment 6, since the ground wire 10a and the overall shield layer 30 are electrically connected, a ground voltage can be obtained at both of them by grounding only one of them. Thus, when only the ground wire 10a is grounded, grounding operation (operation of bundling plural metal wires) for the overall shield layer 30 can be avoided. Alternatively, when both of the ground wire 10a and the overall shield layer 30 are grounded, since they are electrically connected, the ground voltage can be further stabilized.

Figure 3:
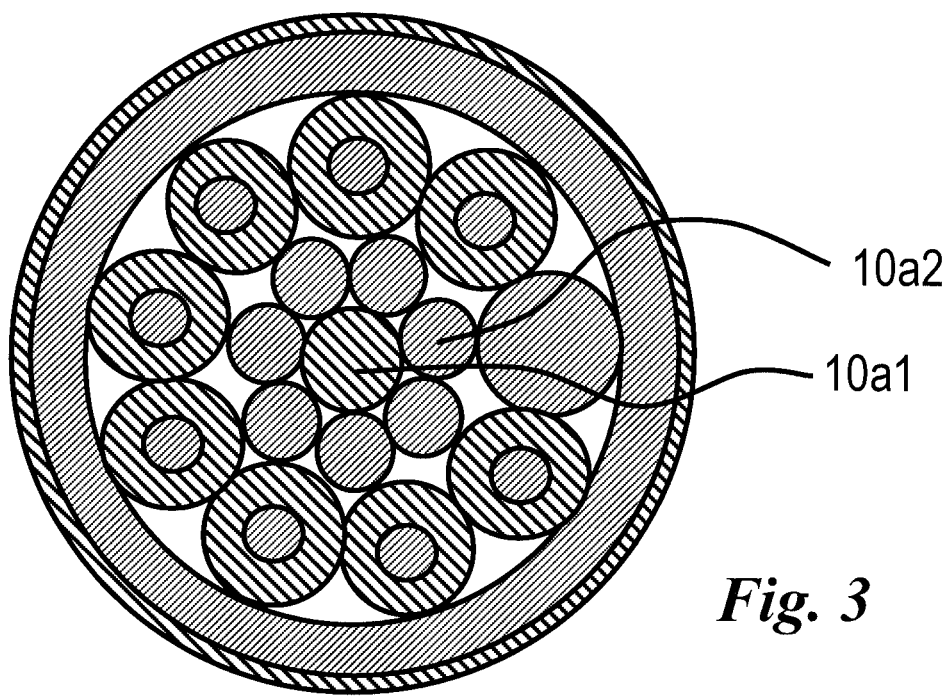
FIG. 3 shows another example of a multi-core cable of Embodiment 6.

The ground wire 10a and/or the conductive wire 20b may be a twisted wire or a single wire. In the case of using the twisted wire, for example, as shown in FIG. 3, the ground wire 10a may be constructed by braiding plural conductor wires 10a2 around a non-conductive filler (made of chemical fiber etc.) 10a1 at a center. Although not shown in the figures, the conductor wire 20b may have the structure similar to the above-illustrated ground wire 10a.

Embodiment 7

Figure 4:
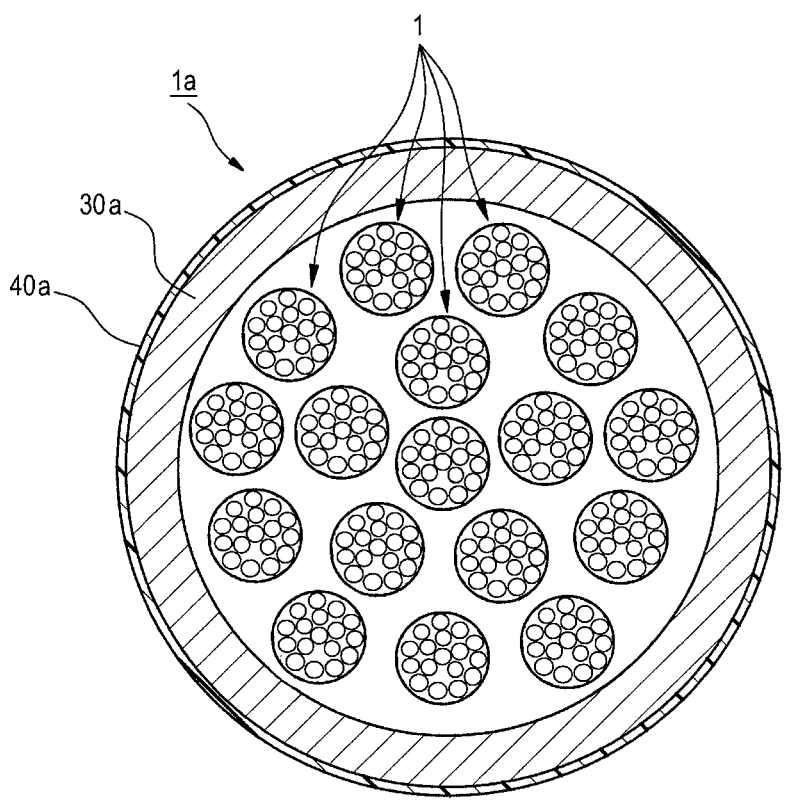
FIG. 4 cross-sectionally shows a multi-core cable of Embodiment 7.

As shown in FIG. 4, a multi-core cable 1a may be formed by collecting the multi-core cable 1 of the above-described embodiments as a wire unit in plurality. The periphery of the plural wire units (multi-core cables 1) is collectively covered with an overall shield layer 30a, and the periphery of the overall shield layer 30a is further covered with a sheath 40a. Also in this multi-core cable 1a, an effect similar to that of the above-described embodiments can be obtained.

Embodiment 8

A multi-core cable of Embodiment 8 will hereinafter be described with reference to the drawings.

As shown in FIG. 5, a multi-core cable 101 of Embodiment 8 includes plural insulated wires 110, a wrapping 120 for bundling the plural insulated wires 110, an overall shield layer 130 which covers the periphery of the wrapping 120, and a sheath 140 which covers the periphery of the overall shield layer is covered.

Each of the insulated wires 110 is constructed of a central conductor 111 and an insulating coating 112 which covers the periphery of the central conductor 111. In Embodiment 8, an AWG 47 (American Wire Gauge number 47) wire is used as the insulated wire 110.

As the central conductor 111 of the insulated wire 110, for example, a twisted wire with an outside diameter of 0.045 mm obtained by twisting three silver-plated copper alloy wires with a conductor diameter of 0.021 mm is used.

As a material of the coating 112 of the insulated wire 110, it is preferable to use a fluorine resin such as a perfluoroalkoxy resin (PFA) with good heat resistance, chemical resistance, non-adhesion, self-lubricity, etc. The coating 112 is formed by, for example, extruding this fluorine resin, and a thickness of the coating 112 is, for example, 0.025 mm and an outside diameter of the coating 112 is, for example, 0.090 mm.

As shown in FIG. 5, in the multi-core cable 101 of Embodiment 8, for example, six insulated wires 110a of the plural (for example, 72 herein) insulated wires 110 are arranged as an internal layer around a center (at a periphery of a center line of the multi-core cable 101) in a cross section perpendicular to a length direction of the multi-core cable 101. The other insulated wires 110b are coaxially arranged in the periphery of the six insulated wires 110a as an external layer. An intervening substance such as aramid fiber or spun rayon yarn may be provided in a gap between the insulated wires 110.

It is preferable to twist the insulated wires 110. In this case, all the insulated wires 110 may be collectively twisted, or the insulated wires 110 may be twisted every insulated wires 110a of the internal layer and insulated wires 110b of the external layer. In the case of being collectively twisted, a relative position of the insulated wires of the internal layer used as a ground wire and the insulated wires 110b of the external layer used as a signal wire can be maintained constant along the length direction of the multi-core cable 101. Accordingly, a positional relationship between the insulated wires 110a, 110b in a cross section perpendicular to the axis of the multi-core cable 101 can be similar in any cross section. A filler may be provided at the center (in FIG. 5, a region surrounded by the six insulated wires 110a) of the insulated wires 110a of the internal layer.

The wrapping 120 is wound on the periphery of the plural insulated wires 110 (110a, 110b) arranged in this manner and thereby, the insulated wires 110 are bundled without destroying its positional relationship. The wrapping 120 is formed by wrapping, for example, a resin tape made of polyester on the periphery of the insulated wires 110.

The periphery of the insulated wires 110 is covered with the overall shield layer 130 through the wrapping 120. The overall shield layer 130 is formed by spirally winding, for example, plural tin-plated copper wires with a conductor diameter of 0.064 mm on the periphery of the insulated wires 110.

The outer periphery of this overall shield layer 130 is covered with the sheath 140. The sheath 140 is formed by wrapping, for example, a resin tape made of polyester on the periphery of the overall shield layer 130. In the multi-core cable 101 of Embodiment 8 including 72 AWG 47 insulated wires 110, an outside diameter of the sheath 140 is, for example, 1.19 mm.

The sheath 140 may be obtained by extruding and coating polyvinyl chloride (PVC), polyolefin or fluorine resin, instead of using a resin tape.

As shown in FIG. 6, in the ends of the multi-core cable 101 of Embodiment 8, terminal processing is performed. That is, the sheath 140, the overall shield layer 130, the insulated wires 110b of the external layer and the insulated wires 110a of the internal layer are sequentially cut with laser processing, thereby exposing the overall shield layer 130, the insulated wires 110b of the external layer, the insulated wires 110a of the internal layer and the central conductors 111 of the insulated wires 110a from the sheath 140 in a stepwise manner.

Then, the central conductors 111 of the plural insulated wires 110a of the internal layer are collectively grounded and also, the end of the overall shield layer 130 is grounded. The insulated wires 110a and the overall shield layer 130 are respectively connected to a ground terminal 24 of a connector etc., as shown in FIGS. 5 and 6, to which the multi-core cable 101 is connected. The insulated wires 110a and the overall shield layer 130 may be connected to the same terminal, or may be connected to different terminals as shown in FIG. 6.

By performing the above-described terminal processing, since the insulated wires 110a of the internal layer and the overall shield layer 130 which covers the periphery of the insulated wires 110a are coaxial, the multi-core cable 101 itself functions as a coaxial cable.

Conductor resistance, insulation resistance and dielectric strength of the multi-core cable 101 were measured.

As a result, the conductor resistance of the multi-core cable 101 was, for example, a maximum of 23000 Ω/Km, and the insulation resistance was 1524 MΩ/Km or more, and the dielectric strength was 150 ACV/min. This means that the multi-core cable 101 of Embodiment 8 has sufficiently practicable electrical characteristics.

On the other hand, in a conventional multi-core cable using a coaxial wire as each core wire, the periphery of insulated wires constructed by covering the periphery of a central conductor with an insulating coating must further be coaxially covered with an external conductor and a protective coating, so that an outside diameter of each core wire (coaxial wire) becomes larger than that of the insulated wire 110 by about 0.1 mm. As a result, when the multi-core cable is formed by collecting the plural coaxial wires, an outside diameter of the multi-core cable is also large.

That is, an outside diameter of an outermost sheath of the conventional multi-core cable including the same number (72) of AWG 47 coaxial wires as the number of insulated wires 110 included in the multi-core cable 101 of Embodiment 8 is, for example, 2.3 mm, and is larger than 1.19 mm of the outside diameter of the multi-core cable 101 of Embodiment 8.

The multi-core cable 101 of Embodiment 8 is smaller in diameter than the conventional multi-core cable using the coaxial wire as each core wire. As a result, handleability of the cable is improved and also, workability in the case of connecting the terminal of the cable to a wiring substrate of a medical device such as an ultrasonograph is improved. Also, a stress for a patient to be treated with an endoscope can be reduced.

Further, the multi-core cable 101 of Embodiment 8 has a pseudo coaxial structure by performing the terminal processing so as to respectively grounding the insulated wires 110a of the internal layer and the overall shield layer 130 which are coaxial, thereby providing good electrical characteristics for practical use in terms of conductor resistance, insulation resistance, characteristic impedance, capacitance, shielding properties, etc.

Although the plural embodiments are described above, the invention is not limited thereto, and other configurations can be adopted as necessary.

For example, the number of insulated wires 110 (110a, 110b) in the multi-core cable 101 of Embodiment 8 is not limited to the above. The multi-core cable 101 can include the necessary number of insulated wires 110 depending on an application.

Although the number of insulated wires 110a of the internal layer is six in Embodiment 8, the multi-core cable 101 can have a coaxial shielding structure as long as at least one insulated wire 110 is arranged in an internal layer and it is grounded at the terminal.

In Embodiment 8, the twisted wire obtained by twisting three silver-plated copper alloy wires is used as the central conductor 111 of the insulated wire 110, but instead of this, a copper alloy wire of a single wire may be used. Also in this case, effect similar to those of Embodiment 8 can be obtained.

In Embodiment 8, as the coating 112 of the insulated wire 110, the fluorine resin such as the perfluoroalkoxy resin (PFA) is used, but the coating 112 may be a foam, and in order to better improve electrical characteristics, for example, a metal tape may be wound on a surface of the coating 112, or the surface may be plated with metal.

The invention claimed is:

1. A multi-core cable arrangement comprising: a plurality of multi-core cables functioning as plural wire units, each of the multi-core cables comprising: at least one ground wire which is arranged in a center in a cross section perpendicular to a length direction of the cable; plural insulated wires arranged in a periphery of the ground wire; an overall shield layer which covers a periphery of the insulated wires, the overall shield layer and the ground wire being coaxial, and the ground wire and the overall shield layer being connected to a ground terminal of a wiring substrate so that the wiring substrate is connected to the multi-core cable; and a sheath which covers a periphery of the overall shield layer; a second overall shield layer which collectively covers a periphery of the plural wire units; and a second sheath which covers a periphery of the second overall shield layer.

2. The multi-core cable of claim 1, wherein the insulated wires are arranged in plural layers so that each layer is coaxial with the ground wire.

3. The multi-core cable of claim 1, wherein
the ground wire is another insulated wire.

4. The multi-core cable of claim 3, wherein at least two of the insulated wires as the ground wires are provided.

5. The multi-core cable of claim 1, wherein
the ground wire is a conductor wire;
another conductor wire and the insulated wires are arranged in a layer around the ground wire; and
the another conductor wire electrically connects the ground wire and the overall shield layer.

6. The multi-core cable of claim 1, wherein:
the at least one ground wire comprises a non-conductive filler disposed at the center and a plurality of conductor wires disposed about the non-conductive filler.

7. The multi-core cable of claim 6, further comprising:
a conductor configured to electrically connect at least one of the conductor wires and the overall shield layer.

* * * * *